United States Patent [19]

Brunerie

[11] Patent Number: 5,705,205
[45] Date of Patent: Jan. 6, 1998

[54] PROCESS FOR THE PRODUCTION OF NATURAL VANILLA EXTRACT BY ENZYMATIC PROCESSING OF GREEN VANILLA PODS, AND EXTRACT THEREBY OBTAINED

[75] Inventor: Pascal Marc Brunerie, Santeny, France

[73] Assignee: Pernod Richard, Paris, France

[21] Appl. No.: 714,513

[22] Filed: Sep. 16, 1996

Related U.S. Application Data

[63] Continuation of Ser. No. 306,729, Sep. 15, 1994, abandoned, which is a continuation of Ser. No. 50,351, filed as PCT/FR92/00837, Sep. 1, 1991, abandoned.

[30] Foreign Application Priority Data

Sep. 3, 1991 [FR] France .................... 91 10873

[51] Int. Cl.⁶ .................... A23L 1/23; C12P 7/00; C12P 7/26
[52] U.S. Cl. .................... 426/44; 420/52; 420/425; 420/518; 420/534; 420/538; 420/629; 420/650; 435/132; 435/148
[58] Field of Search .................... 426/44, 52, 425, 426/518, 534, 538, 629, 650; 435/132, 148

[56] References Cited

U.S. PATENT DOCUMENTS 2,835,591  5/1958  Graves et al. .................... 426/44

FOREIGN PATENT DOCUMENTS

| | | |
|---|---|---|
| 0 332 281 | 9/1989 | European Pat. Off. . |
| 0 416 713 | 3/1991 | European Pat. Off. . |
| 1 156 084 | 12/1958 | France . |
| 2 443 265 | 7/1980 | France . |
| 2 625 750 | 7/1989 | France . |
| 2 634 979 | 2/1990 | France . |
| 9325088 | 12/1993 | WIPO . |

OTHER PUBLICATIONS

World Patents Index Latest, Derwent Publications, Vanilla Flavour Obtain Culture Yeast Lactic Acid Bacteria Medium Contain Vanilla Bean, Section Ch, Week 8316 & JP-A-58 043 757, Hasegawa 14 Mars 1983.

Food Research, F.E. Arana, Action of a beta-glucosidase in the curuing of vanilla, 1943, pp. 343-351.

W. Pigman, The Carbohydrates Chemistry, Biochemistry and Physiology, Academic Press, 1957 pp. 536-589.

*Primary Examiner*—Esther Kepplinger
*Assistant Examiner*—Curtis E. Sherrer
*Attorney, Agent, or Firm*—Foley & Lardner

[57] ABSTRACT

A process for increasing the yield of natural vanilla flavor. Green vanilla pods are hydrated. The resulting hydrated pods are ground, forming a liquid phase and a solid phase. The resulting ground hydrated product of green vanilla pods is treated with an enzymatic system including at least one enzyme. The enzyme system possesses from about 10 to about 1000 units of beta-glucose activity per gram of green vanilla pods. The ground hydrated green vanilla pods and the enzymatic system are incubated at a temperature of from about 10° C. to about 40° C. for a period of between about 2 hours and about 30 hours sufficient to allow the release of the vanilla flavor. The liquid phase containing the vanilla flavor is separated from the solid phase.

12 Claims, 2 Drawing Sheets

PROCESS FOR THE PRODUCTION OF NATURAL VANILLA EXTRACT BY ENZYMATIC PROCESSING OF GREEN VANILLA PODS, AND EXTRACT THEREBY OBTAINED

This application is a continuation of application Ser. No. 08/306,729, filed Sep. 15, 1994, now abandoned which is a continuation of Ser. No. 08/050,351, filed Apr. 30, 1993, now abandoned which is the National Phase of PCT/FR92/00837, filed Sep. 1, 1992.

The present invention relates to a process for the production of natural vanilla flavor by enzymatic treatment of the green vanilla pods. It also relates to the flavor obtained by the process.

BACKGROUND OF THE INVENTION

Vanilla flavor mainly comprises, as constituents, vanillin, vanillic acid, para-hydroxybenzoic acid and para-hydroxybenzaldehyde. These constituents are practically absent from the green pod, even when mature, and they are formed only slowly in the pod after harvesting.

At the industrial level, vanilla extracts (comprising especially the various constituents listed above) are obtained from pods which have been successively subjected, in the usual manner, to scalding, that is to say an immersion in water at 65° C. for 3 minutes, to drying during which the pods lose their water and become brown in color, and to a final curing stage. Such a treatment extends over a period of about 9 months during which many assessments of the quality of the pods are carried out, thus increasing its cost [Mémento de l'agronomie, 4th Edition, Ministère de la coopération et du développement (Ministry of Overseas Affairs and Development)]. Such a process makes it possible to obtain between 20 and 30 g of vanilla flavor per kilogram of pod dry matter content.

The development of the vanilla flavor during this treatment is partly due to the hydrolysis of a glucosylated precursor, glucovanillin, which occurs in the green pod at a level such that 50 g of vanillin may be obtained during its slow hydrolysis during the curing (Arana, F.E., 1943, Food Research, vol. 8, pages 343–351). Microbial or enzymatic decomposition of the vanillin is probably responsible for the substantial loss observed during this treatment.

In order to overcome the disadvantages associated with this process, it has already been proposed by Patent FR-A-2,634,979 to freeze the green pods at a temperature of between −5° C. and −30° C. and then to reheat them before extracting the flavor constituents therefrom. This process makes it possible to shorten the curing time.

One object of the present invention is to provide a new process which makes it possible to release vanillin and the other flavor constituents, contained in the form of glucosides, in the green pod.

SUMMARY OF THE INVENTION

Another object of the present invention is to provide a process which makes it possible to produce a vanilla flavor with an excellent yield.

According to the present invention, in the process for the production of natural vanilla flavor, a ground product of green vanilla pods is treated by means of an enzymatic system capable of destroying the membrane systems of plant cells and of hydrolyzing the glucosides.

The fact that a ground product is used makes it possible to facilitate the enzymatic attack of the cell membranes. It is therefore clear that the finer the grinding, the more the enzymatic attack will be facilitated given, naturally, the constraints associated with the industrial implementation of such a process. Green vanilla pods are understood to mean ripe pods which have been freshly harvested. In general, the process should be carried out a few days following the harvest, generally between 1 and 12 days following it. Moreover, the use of the crude ground product avoids any prior extraction stage.

An enzymatic system capable of destroying the membrane systems of plant cells is understood to mean all the systems which can liquefy fruits, vegetables and in general all plant cells which can be used as foodstuff.

Advantageously, particularly effective enzymatic systems will be used to liquefy the green vanilla pods.

DESCRIPTION OF THE PREFERRED EMBODIMENT(S)

Figure 1:
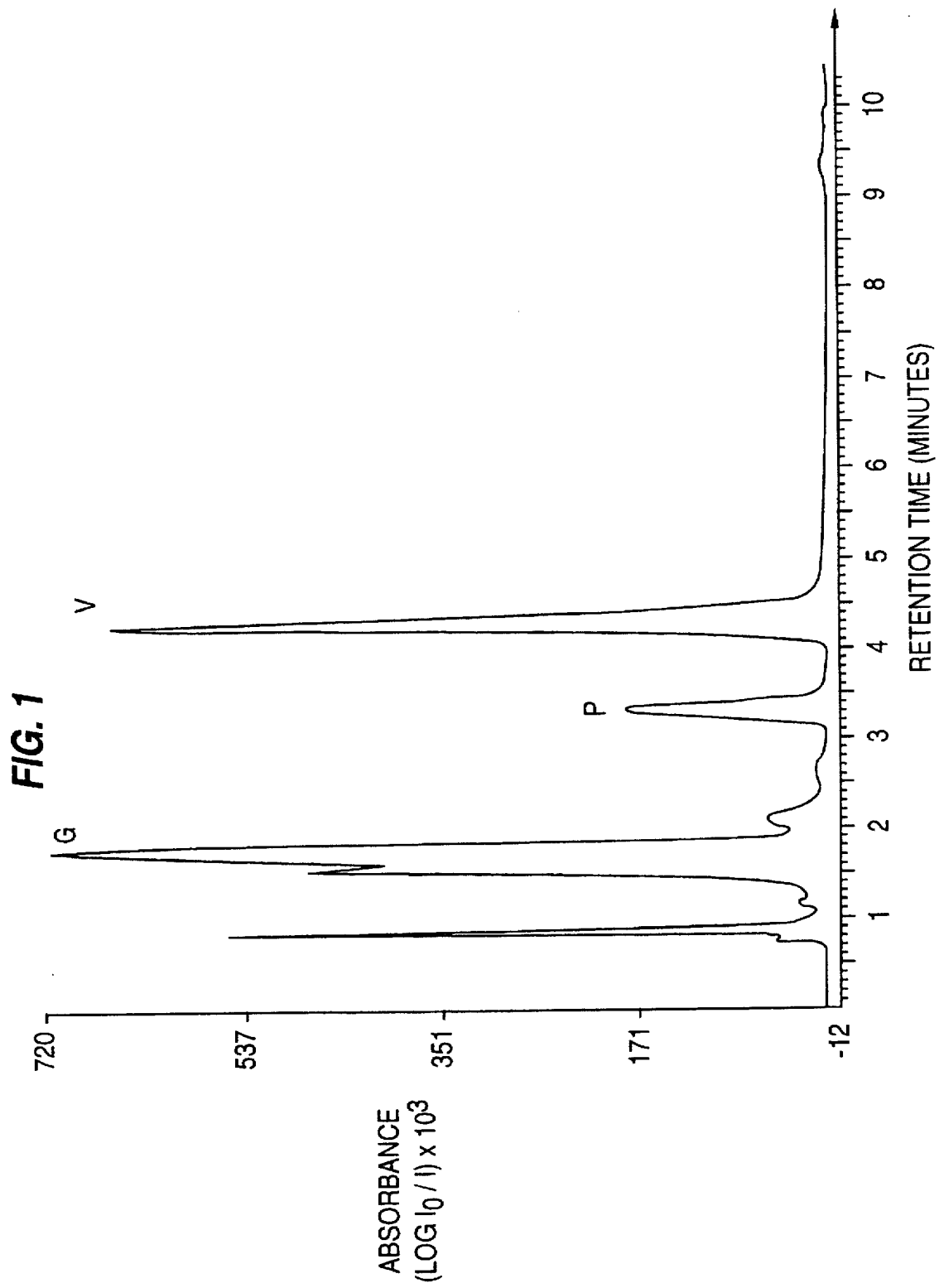
FIG. 1 is a chromatogram of a ground product of green vanilla pods after incubation for 20 hours without enzymes.

Generally, there may be used one or more enzymatic preparations chosen from pectinases, cellulases, hemicellulases or celliobiases, which possess one or more glucosidase activities. These enzymes may be used alone or in a mixture.

Preferably, the enzymatic system should comprise one or more enzymes which possess a glucosidase, and especially a beta-glucosidase, activity. These enzymes are well known to persons skilled in the art and many systems based thereon are commercially available.

Generally, it is clearly understood that the invention covers all the enzymatic systems, and especially those having a glucosidase activity, which make it possible to release the vanilla flavor potentially contained in the green vanilla pods. Persons skilled in the art will be able, using simple procedures (such as those for example illustrated in the examples which will be described following the present description), to choose the enzymatic systems which are appropriate.

Preferably, the green vanilla pods are treated with an enzymatic system which comprises: (a) at least one enzyme capable of destroying the cell membrane systems of plant cells and is selected from an enzyme having pectinase activity and enzyme having cellulase activity and an enzyme having hemicellulase activity and mixtures thereof and (b) at least one enzyme possessing from about 10 to about 1000 units of a beta-glucosidase activity per gram of vanilla pods.

According to an advantageous characteristic of the process according to the invention, and in order to facilitate the grinding, the green pods are hydrated and then ground. Generally, without being an essential feature of the present invention, the quantity of water which can be added will be equivalent to the weight of the plant material. Advantageously, the ground product is centrifuged, filtered and rediluted with ethyl alcohol.

The enzymatic system advantageously comprises 10 to 1000 units of beta-glucosidase activity per gram of green vanilla pods, and preferably from 20 to 500 units of beta-glucosidase enzymatic activity. It was observed that a range of between 40 and 400 units of enzymatic activity was even more advantageous for implementing the process according to the invention.

The incubation is carried out at a pH which is advantageously between 3 and 7, and preferably 4 and 6 and even more advantageously about 5. The natural pH of the ground product obtained being equal to 5, this ground product is therefore naturally at the optimal value.

Also preferably, the process is carried out with stirring for a period sufficient to allow the release of the vanilla flavor. Advantageously, this period will be greater than 2 hours at room temperature. This temperature can be increased or decreased while being careful, on the one hand, not to exceed a maximum temperature which can result in degradation of the vanilla flavor and, on the other hand, not to decrease the temperature too substantially, thereby running the risk of blocking the desired reactions. The temperature will be generally between 10° and 60° C., preferably between 30°–40° C.

Advantageously, the period of incubation will be between 3 and 30 hours. However, it was observed that the release was generally complete after a few hours of incubation, it being possible for persons skilled in the art to determine the latter by means of high performance liquid chromatography analyses. It is normally advisable not to exceed 24 hours.

After incubation, the liquid phase containing the vanilla flavor is separated from the solid phase containing especially the insoluble cell residues. This separation may be carried out for example by filtration and/or by centrifugation.

The liquid phase containing the natural vanilla flavor may then be used either directly or after concentration of the flavor extract. This concentration may be carried out by evaporation, optionally under vacuum, and then filtration. It may also be carried out by extraction with solvent and subsequent evaporation of the latter. The examples below illustrate the invention without however limiting it:

According to a general procedure, the green pods, after harvesting, are ground in a mixer after addition of a quantity of water equivalent to the weight of the plant material. The incubation with the enzymes is carried out at the natural pH of the ground product obtained, that is to say at a pH of about 5, with stirring.

At the end of the reaction, 96% alcohol is added so as to obtain a 50% aqueous-alcoholic medium. The sample is then filtered.

EXAMPLE 1

Tests on Various Enzymatic Systems

Various types of industrial enzymatic preparations were tested so as to select therefrom one or more possessing a high glucosidase activity and whose specificity could make it possible to release vanillin and the other volatile constituents.

The tests are carried out using the following enzymatic systems (the symbol u is the glucosidase activity unit):

```
A: without enzymatic system (control)
B: pectinase and beta-glucosidase         50 µ/mg
C: pectin glucosidase and cellulase       17 µ/mg
D: pectin glucosidase                     79 µ/mg
E: pectinase and hemicellulase            4455 µ/mg
```

After incubation, the ground product is centrifuged. The analysis and the determination of the quantity of vanillin are carried out by liquid chromatography (HPLC) on the supernatant.

The results obtained are presented in the table below:

| Type of enzyme | Control without enzyme | A | B | C | D | E |
|---|---|---|---|---|---|---|
| Quantity of vanillin in g/kg of plant material | 0.355 | 0.319 | 1.3 | 3.19 | 1.5 | 6.5 |

Enzyme E is a pectinase which is normally used for the liquefaction of fruit juices, it is the one most suitable for our process. Indeed, its liquefying properties make it possible to destroy the membrane systems of the plant cell, thus releasing the cytoplasmic contents and enabling the glucosidase activity which it contains to be expressed.

EXAMPLE 2

Number of Enzyme Units

The optimum quantity of enzymatic preparation for releasing the flavor was determined. This activity is determined at 30° C. in a citrate phosphate buffered medium, pH=5, using p-nitrophenyl glucoside as substrate, on the enzymatic system E, one unit of activity corresponding to the hydrolysis of one micromole of substrate per minute.

The results are indicated in the table below:

| Quantity of enzymes in activity unit/kg of green pods × $10^3$ | 0 | 90 | 220 | 310 | 450 |
|---|---|---|---|---|---|
| Quantity of vanillin in g/kg of green pods obtained after 20 h of incubation | 1.5 | 2.9 | 3.5 | 3.6 | 3.5 |

This table shows that the optimum activity is situated around 220 units of enzymatic activity for 1 g of green pod used.

EXAMPLE 3

Duration of Incubation

Various samplings were carried out over time so as to determine the incubation time required for the production of a maximum level of free vanillin in the medium. To 50 g of green pods ground in 50 cc of water, are added $12 \times 10^3$ units of glucosidase activity (system E). The results below show that the maximum quantity of free vanillin in the medium is reached after about 7 hours of incubation.

| | Incubation at 30° C. | | | | | | |
|---|---|---|---|---|---|---|---|
| Incubation time | T0 | 1 h | 2 h | 4 h | 8 h | 10 h | 25 h |
| Quantity of vanillin in g/kg | 1.1 | 1.4 | 1.7 | 2.2 | 2.9 | 3.2 | 3.4 |

| Incubation at 37° C. | | | | | | |
|---|---|---|---|---|---|---|
| Incubation time | T0 | 1 h | 2 h | 4 h | 6 h | 25 h |
| Quantity of vanillin in g/kg | 1.1 | 2.3 | 2.9 | 3.6 | 3.9 | 4 |

Figure 2:
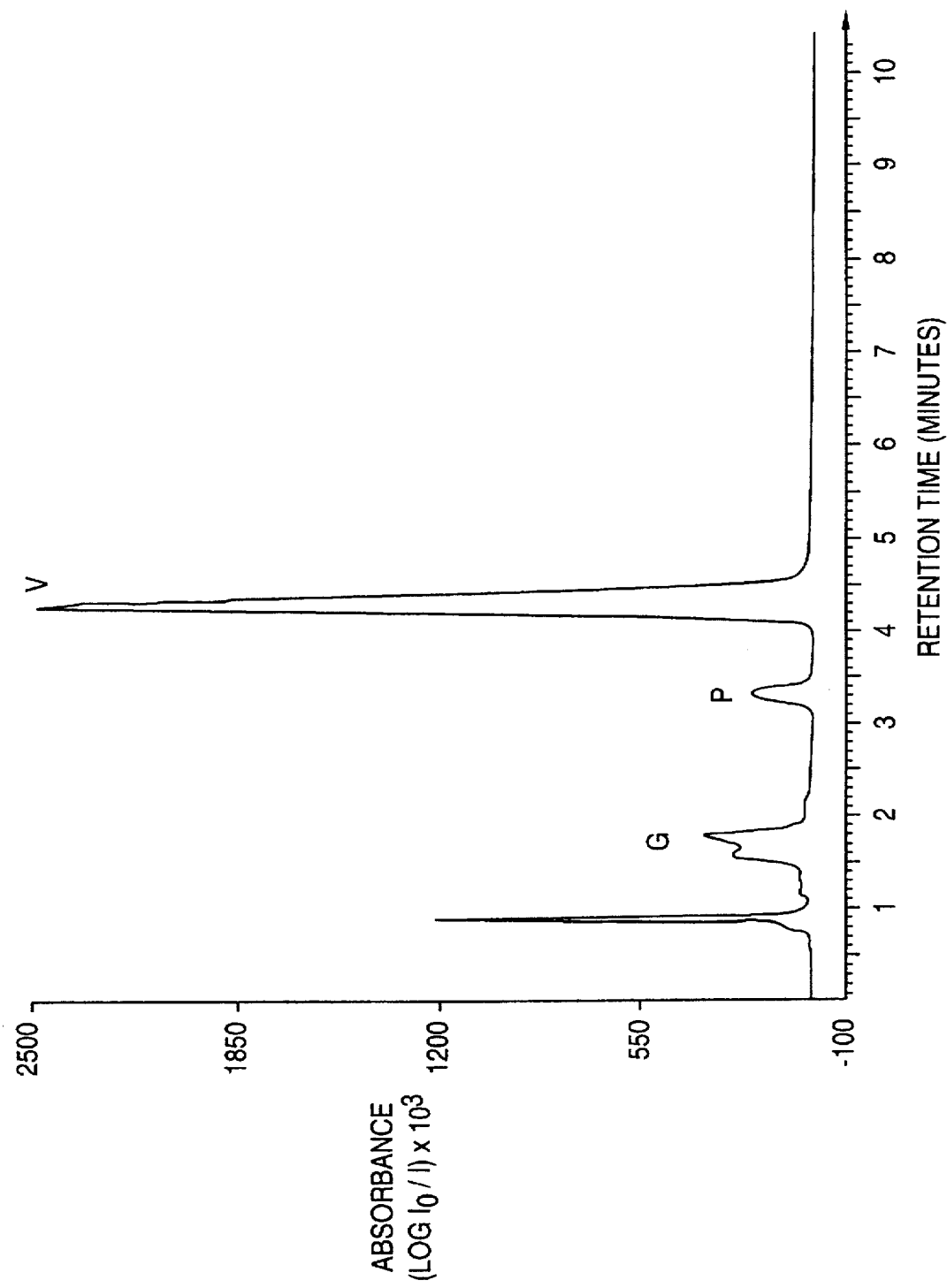
FIG. 2 is a chromatogram of a ground product of green vanilla pods after incubation for 20 hours in the presence of enzymes.

The appended FIGS. 1 and 2 illustrate, for the last example, the chromatogram obtained after 20 hours without enzymatic system (FIG. 1) and with enzymatic system (FIG. 2).

The analytical methods were the following for the examples above:

96% alcohol is added so as to obtain a 50% aqueous-alcoholic medium.

The sample medium is filtered and directly injected by HPLC.

Apparatus:
Hewlett Packard 1090, UV detector
Column: Hewlett Packard ODS Hypersil
Solvent A: citrate phosphate buffer,
pH: 4.66
Solvent B: acetonitrile
Flow rate: 0.3 ml/min
Absorption at 300 nm

| Gradient: | T0: 0% of solvent B |
|---|---|
| | 10': 15% of solvent B |
| | 15': 80% of solvent B |
| | 20': 10% of solvent B |

The appended FIGS. 1 and 2 are chromatograms of ground product of green pods.

FIG. 1:
Chromatogram at 300 nm of the ground product of green pods, control without enzymes. G: glucovanillin, V: vanillin P: para-hydroxybenzaldehyde FIG. 2:
Chromatogram at 300 nm of the ground product of green pods, after 20 h of incubation in the presence of enzyme: G: glucovanillin, V: vanillin P: Para-hydroxybenzaldehyde.

I claim:

1. A process for preparing vanillin from vanilla beans which comprises:
   a) hydrating green vanilla pods;
   b) grinding the resulting hydrated pods to form a ground hydrated product having a liquid phase and a solid phase;
   c) treating said ground hydrated product with an enzymatic system which comprises: (a) at least one enzyme capable of destroying the cell membrane systems of plant cells and wherein said enzyme is selected from the group consisting of an enzyme having pectinase activity, an enzyme having cellulase activity, an enzyme having hemicellulase activity and mixtures thereof and (b) at least one enzyme possessing from about 10 to about 1000 units of a beta-glucosidase activity per gram of green vanilla pods;
   d) incubating said ground hydrated product containing said enzymatic system at conditions of a temperature of from about 10° C. to about 40° C. for a period of from about 2 hours to about 30 hours, said conditions being sufficient to enzymatically breakdown cell membranes of said ground hydrated product and allow the release of the vanillin;
   e) separating the liquid phase from the solid phase and;
   f) recovering said liquid phase which contains the vanillin and other soluble material.

2. The process as claimed in claim 1 wherein the ground hydrated product has a pH between 3 and 7.

3. The process as claimed in claim 1, wherein the period of incubation of the mixture of ground product and the enzymatic system is between 3 and 30 hours.

4. A process according to claim 1; further comprising:
   g) isolating the vanilla flavor from the liquid phase.

5. A process according to claim 1, wherein the at least one enzyme (a) is a cellulase.

6. A process according to claim 2, wherein the pH of the liquid phase is about 5.

7. A process according to claim 1,wherein the at least one enzyme (b) possesses 20 to 500 units of beta-glucosidase activity per gram of green vanilla pods.

8. A process according to claim 1, wherein the at least one enzyme (b) possesses 40 to 400 units of beta-glucosidase activity per gram of green vanilla pods.

9. A process according to claim 1, wherein said ground hydrated product and said enzymatic system are incubated at a temperature of from about 30° C. to about 40° C.

10. The process as claimed in claim 5, wherein the at least one enzyme (b) possesses 20 to 500 units of beta-glucosidase activity per gram of green vanilla pods.

11. The process as claimed in claim 5, wherein the ground hydrated product has a pH of the liquid phase is between 3 and 7.

12. The process as claimed in claim 5, wherein the period of incubation of the mixture of ground product and the enzymatic system is between 3 and 30 hours.

* * * * *